United States Patent [19]

Hadden

[11] Patent Number: 4,489,590

[45] Date of Patent: Dec. 25, 1984

[54] METHOD AND APPARATUS FOR GAS DETECTOR CALIBRATION

[75] Inventor: David M. Hadden, Los Altos, Calif.

[73] Assignee: Delphian Corporation, Sunnyvale, Calif.

[21] Appl. No.: 342,048

[22] Filed: Jan. 25, 1982

[51] Int. Cl.³ ............................................ G01N 37/00
[52] U.S. Cl. ..................................................... 73/1 G
[58] Field of Search ......................................... 73/1 G

[56] References Cited

U.S. PATENT DOCUMENTS

| | | | |
|---|---|---|---|
| 3,729,979 | 5/1973 | Wiberg | 73/1 G |
| 4,177,667 | 12/1979 | Rolf | 73/1 G |
| 4,205,550 | 6/1980 | Swanson | 73/1 G |
| 4,279,142 | 7/1981 | McIntyre | 73/1 G |

Primary Examiner—S. Clement Swisher
Attorney, Agent, or Firm—Fitch, Even, Tabin & Flannery

[57] ABSTRACT

Methods and apparatus for applying calibrating gas to a combustible gas sensor, in which a calibration enclosure is formed mechanically upon application of pressurized calibration gas.

8 Claims, 4 Drawing Figures

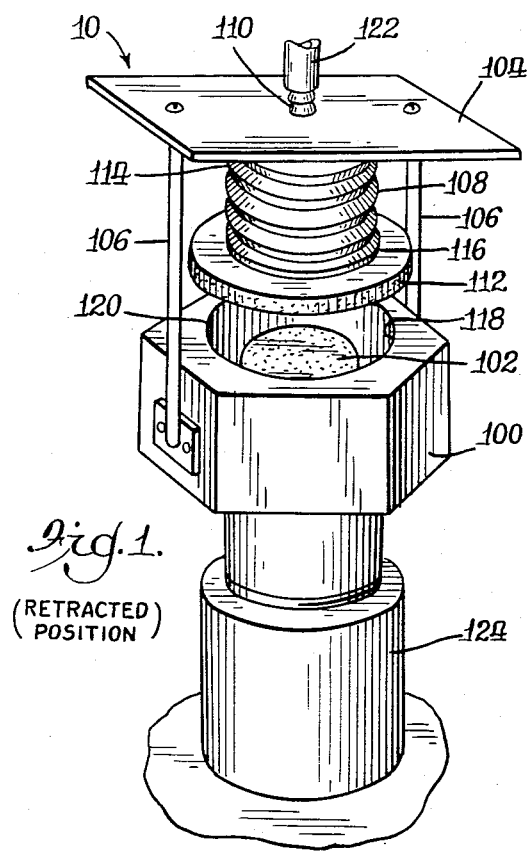
Fig. 1. (RETRACTED POSITION)
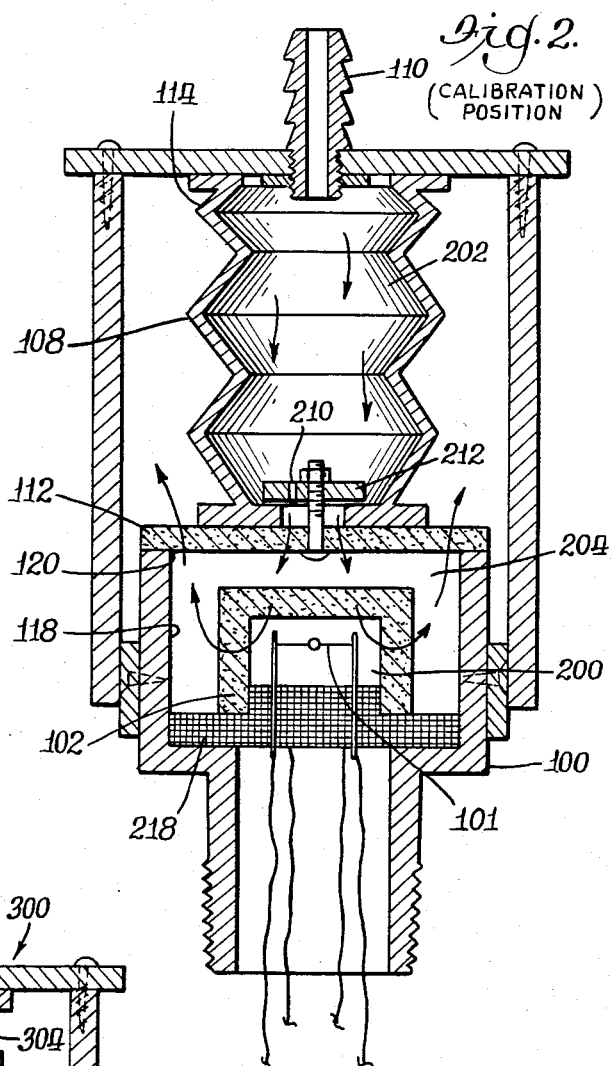
Fig. 2. (CALIBRATION POSITION)
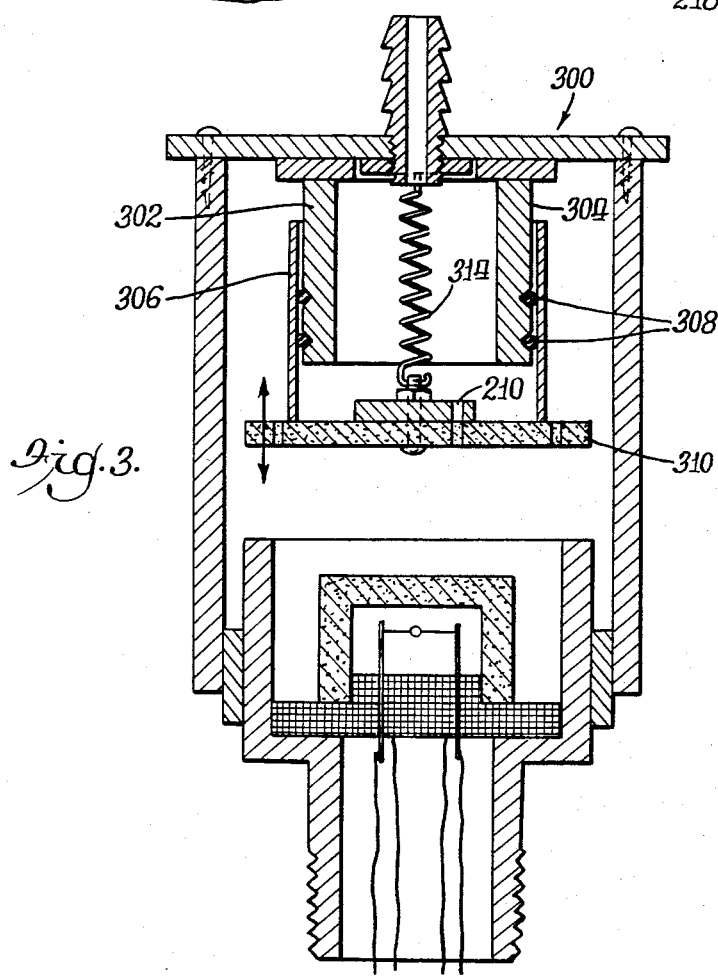
Fig. 3.
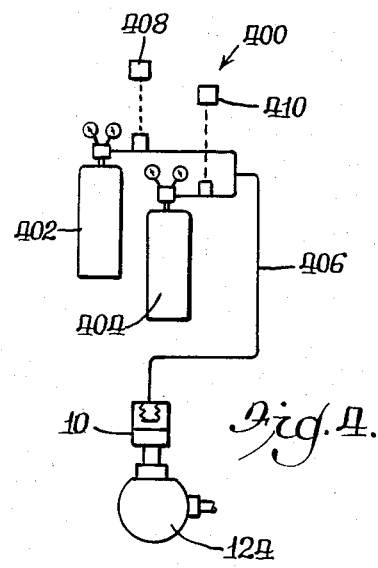
Fig. 4.

METHOD AND APPARATUS FOR GAS DETECTOR CALIBRATION

Generally, the present invention is directed to combustible gas detection systems, and, more particularly, is directed to methods and apparatus for calibration of combustible gas detectors.

It is customary to periodically calibrate the zero and span performance of combustible gas sensors in order to reconfirm or reestablish their measurement accuracy. Calibration of the sensor elements of combustible gas detectors is important to achieving accurate measurement from the sensors, because most sensors tend to have some zero drift over time in either the positive or negative direction, even when no combustible hydrocarbons are present. This zero drift of the sensor elements over time may be compensated for or adjusted in accordance with conventional practice, by periodic zero calibrations utilizing a known calibration gas composition, which will generally be a gas such as synthetic air containing no hydrocarbons or other combustible gases. A similar problem exists with respect to the sensor span signal. Combustible hydrocarbon sensors also have a tendency to slowly lose sensitivity with time, so that the span, or range of response from the zero baseline response for a given combustible gas concentration, decreases over the useful life of the sensor. This loss of sensitivity may similarly be corrected for or adjusted by periodic span calibrations of the sensor circuitry utilizing a gas with a predetermined combustible gas concentration, in order to establish a desired proportionality between the output signal and the combustible gas concentration monitored by the sensor device.

In certain types of gas detection sensors, it is desirable to be able to apply calibration and zero gas automatically to the sensor. For example, combustible gas sensors may be placed in locations that are difficult to reach for manual calibration during routine calibration cycles. It may also be desirable to control the calibration from a remote location or controller system whether or not the sensor is placed in an inconvenient or inaccessible location. However, there are substantial limitations placed on the types of remotely operating mechanisms which may be utilized because of the potentially hazardous atmosphere at the sensor site. Specifically, such mechanisms should not only be rugged and reliable for use in the field environment, but also should be explosion-proof or intrinsically safe.

One technique which has been used to apply calibration gas to combustible gas detectors is described in U.S. Pat. No. 3,421,362, in which calibration gas is applied under pressure to a zone between inner and outer porous flame arresters. However, this technique does not guarantee that adequate calibration is accomplished under environmental conditions in which the outer flame arrester, or dust cover, may become clogged with dust, dirt, oil vapors or other contaminants. In this regard, because some combustible gas sensors may have life expectancies of two or more years, and are often used in very contaminated areas, it is possible that the outer flame arrester may become clogged to the extent that only a limited amount of gas from the ambient environment can diffuse therethrough to the internally positioned sensing element. Moreover, porous flame arrester elements may also lose permeability due to chemical corrosion. In this regard, some flame arresters are made of metals which may be chemically attacked by reactants in the sensor environment. The result is that the compounds formed by reaction of the flame arrester with such reactants will clog the pores of the flame arrester and thereby severely alter the performance characteristics of the enclosed detector elements. Because calibration gas is applied in the zone between inner and outer porous caps under a pressure greater than atmospheric pressure, the calibration gas may be forced into the sensor detector cavity under pressure, particularly when such caps have diminished permeability. The result is that a substantially larger quantity of calibration gas per unit time may be forced into the detector cavity than would occur under conditions of diffusion under ambient conditions of normal operation. This is disadvantageous because various sensors, such as catalytic combustible bead or catalytic combustible hot wire sensors, consume or react with the gases they are designed to detect. The result is that during calibration enough gas may be forced into the sensor chamber due to the pressure differential between the applied calibration gas, and the normal ambient pressure, that the sensor may erroneously appear to give an appropriate response under the pressurized calibration conditions, or may be calibrated to have an erroneously low sensitivity to combustible gases in the ambient environment under normal operations conditions which provide only for diffusion transfer of ambient gases. A sensor exposed under normal operative conditions to the same concentration of combustible gas as used for calibration may then give a substantially lower reading due to the more limited amount of combustible gas reaching the sensor under operating conditions as contrasted to the higher pressure calibration conditions. This, of course, may be a source of substantial danger if, for example, a sensor is miscalibrated to provide a response that is substantially lower than the true ambient combustible gas concentration.

Accordingly, there is a need for improved calibration systems for combustible gas sensors, and it is an object of the present invention to provide improved methods and apparatus for applying calibration gases to sensors for combustible gases or other hazardous materials. It is a further object to provide such methods and apparatus which are intrinsically safe at the sensor site environment. These and other objects of the present invention will become more apparent from the following detailed description and the accompanying drawings, of which:

FIG. 1 is a perspective view, partially broken away, of an embodiment of an automatically calibrating combustible gas sensor assembly in accordance with the present invention, which is shown in its retracted position;

FIG. 2 is a cross sectional view of the sensor assembly of the embodiment of FIG. 1, which is shown in its calibration position;

FIG. 3 is a cross sectional view of an alternative embodiment of an automatically calibrating combustible gas sensor assembly like that of FIG. 2; and;

FIG. 4 is a schematic illustration of the embodiment of FIG. 1 in association with means for supplying zero and span gas for calibration of the sensor elements.

Generally in accordance with the present invention, methods and apparatus are provided for the application of calibration gas to combustible gas detectors. By "calibration gas" is meant a gas of known composition which may be used to test the response of a combustible gas sensor. Calibration gases include "zero" calibration gases (preferably air) having substantially no combustible gas components, which accordingly may be utilized to establish sensor baseline response, and "span" calibration gases comprising a predetermined quantity of one or more combustible gas components which may be used to test the sensor sensitivity. Desirably, the combustible gas component or components utilized in the span calibration gas will be the same as or similar to the combustible gas or gases which may be expected to be in the environment monitored by the combustible gas sensor to be calibrated.

In accordance with apparatus aspects of the present invention, calibrating gas sensor assemblies are provided which are mechanically responsive to the application of pressurized calibration gas for the temporary formation of an enclosed calibration gas zone surrounding the sampling surface of a combustible gas detector which is normally exposed to the ambient atmosphere intended to be monitored. In this regard, apparatus in accordance with the present invention generally comprises a combustible gas sensor assembly itself comprising one or more combustible gas sensor elements and a gas permeable housing forming a detection chamber for the sensor elements and which is adapted to permit transfer of gases between the detection chamber and the atmosphere external to the detection chamber without permitting the passage of a flame, ignition or combustion wave fronts therethrough. The gas permeable surface(s) of combustible gas sensor assembly will normally be exposed to the ambient atmosphere to be monitored, but upon calibration of the instrument will be effectively enclosed by a calibration chamber formed in response to application of calibration gas as will be more fully described hereinafter. The combustible gas sensor assembly will desirably include a combustible gas sensor element and a matched reference element which form the measurement and reference components of a bridge circuit in accordance with conventional practice. The housing for the gas sensor and reference elements will desirably comprise a non-permeable base portion partially enclosing and forming a mounting support for the one or more sensor elements, and a porous, gas permeable surface completing the enclosure of the sensor elements. The porous enclosure surface may be formed of a porous, sintered metal in accordance with conventional practice in the manufacture of combustible gas detector flame arrester elements.

An important aspect of the present apparatus is the provision of calibration zone enclosure forming means which is mechanically responsive to the application of pressurized calibration gas for forming a calibration gas enclosure surrounding the sampling surface of the combustible gas sensor assembly, and for exposing the sampling surface to the ambient atmosphere upon ceasing the application of pressurized calibration gas.

The calibration zone enclosure forming means does not form a calibration zone unless pressurized gas is applied to the forming means and upon removal of the pressurized calibration gas the temporarily formed calibration enclosure is opened so that the sampling surface of the sensor assembly is again exposed to the ambient atmosphere. The calibration apparatus further includes means for conducting calibration gas through the calibration zone formed by the calibration zone forming means, so that the sampling surface of the sensor assembly is surrounded by substantially only the calibration gas. Desirably, the calibration gas conducting means will comprise means such as one or more flow regulation orifices for introducing calibration gas at a predetermined rate into the temporarily formed calibration zone, and means for permitting the exit of gas introduced into the calibration zone. Desirably, the calibration gas may be conducted through the calibration zone without substantially increasing the pressure in the zone above ambient pressure.

The apparatus may further include means for applying a desired calibration gas at a predetermined pressure to the enclosure forming means in order to carry out sensor calibration, as will be more fully described hereinafter.

In accordance with method aspects of the present invention, a sensor calibration may be carried out utilizing a desired calibration gas by applying the calibration gas to the sensor assembly at a predetermined pressure, which will desirably be in the range of from about 3 to about 50 psig, and preferably in the range of from about 5 to about 30 psig, and forming an calibration zone effectively enclosing the sensor sampling surface in mechanical response to the application of the pressurized calibration gas. Also in accordance with the calibration method, the calibration gas is introduced into and through the calibration zone thus formed, under predetermined flow conditions. Desirably, the calibration flow delivery rate will be in the range of from about 0.5 and about 3 liters per minute for preferred embodiments of the present invention, and the pressure in the calibration zone should not best exceed the ambient pressure by more than about 5 psi. However in accordance with the present invention, the calibration gas may be advantageously introduced into the calibration zone at relatively lower pressure, and in this regard, it is particularly preferred that the pressure in the calibration zone not exceed the ambient pressure by more than about 0.5 pounds per square inch. Calibration may be carried out for example, by introducing the calibration gas into the temporarily formed calibration zone such that the enclosure has a pressure of about 3 inches of water in respect to the ambient pressure outside the zone.

In this regard, it is noted that in normal operation the sampling cell functions by a diffusion mechanism in accordance with which gases, including any combustible gas, from the ambient environment, diffuses sintered metal flame arrester into the sampling zone immediately surrounding the sensor elements, and combustion byproducts similarly diffuse from the sampling zone through the flame arrester into the ambient atmosphere. It will be appreciated that pressure variations during calibration are undesirable and may lead to pressurized introduction of calibration gas through the porous flame arrester to the sampling zone in a manner which is not diffusion-controlled.

It is also desirable that adequate flow of calibration gas be maintained, as previously indicated, to the calibration zone, particularly in respect to "span" calibration gas having a combustible gas component, to remove continually diffused calibration products and to provide for accurate calibration in a manner simulating conditions of the ambient environment.

The calibration gas flow through the calibration zone is continued at least until the composition of gas in the zone is substantially the composition of the calibration gas, and until stabilization of the sensor output, which desirably will occur within about one and one-half minutes, depending on the performance characteristics of the sensor assembly and sensor elements.

After calibration of the sensor elements, the application of calibration gas is stopped, and the access of the sampling surface to the ambient atmosphere is restored. Because it is generally desirable to calibrate the sensor elements first with a zero calibration gas, and subsequently with at least one span calibration gas, the application of the calibration gases may be carried out sequentially, it being noted that it is not necessary to restore the access of the sampling surface to the ambient atmosphere until the completion of the calibration sequence.

Having generally described various of the aspects of the present methods and apparatus, the invention will now be more particularly described with respect to the specific embodiments shown in FIGS. 1–4 of the drawings.

Illustrated in FIG. 1 is an embodiment automatic calibration assembly 10 which is shown in its normal, retracted position in which the porous combustible gas sensor sampling surface is exposed to the ambient atmosphere for monitoring of the environment, prior to application of pressurized calibration gas. The assembly 10 is shown in perspective view, partially broken away from a calibration gas supply conduit 122 and an explosion-proof terminal housing 124 which encloses circuitry for the operation of the combustible gas and reference sensor elements of the device 10. The gas and reference sensor circuitry and housing therefor may be of conventional design, and preferably may in accordance with system described in U.S. Pat. No. 4,305,724 issued Dec. 15, 1981 which is hereby incorporated by reference. The device 10 is further illustrated in cross sectional view in FIG. 2 to disclose the internal construction of the sensor and application gas calibration mechanisms. The device 10 is shown in operative, schematic connection with calibration gas control apparatus in FIG. 4.

As shown in FIG. 1, the device 10 comprises a sensor housing 100 which encloses a combustible gas sensor element and a matching reference element adapted for the catalytic combustion detection of combustible gas. The housing 100 may be formed of any suitable material, and is conveniently machined from aluminum, steel or stainless steel bar stock to have a threaded base for assembly with the terminal box 124, and an upper cavity 118 for containing the various sensor components. The catalytic gas sensor and reference elements are enclosed in a sensing zone 200 (FIG. 2) defined by a gas impermeable base plate 218 and a gas permeable flame arrester 102 such that combustible gas in the atmosphere surrounding the housing 100 diffuses through the sintered metal flame arrester 102 for detection in the zone 200. The arrester cap 102 prevents ignition of a combustible atmosphere surrounding the auto calibration fixture embodiment 10 as might occur from electrical failure of the sensor element or related circuitry, while permitting permeation of ambient gas therethrough for analysis. The flame arrester 102 and its enclosed sensing zone 200 are positioned in a recess 118 formed in the housing 100, but are there normally exposed to the ambient environment, except during the calibration mode of the device 10. In this regard, a mounting plate 104 is supported above the housing 100 by means of supports 106, and attached to the mounting plate is a bellows 108 which is adapted to travel along an axis generally aligned between its distal end 114 and its proximal end 116 toward the recess 118 and flame arrester 102. At the proximal end 116 of the bellows 108, a sintered metal diffusion disk 112 is provided which is of sufficient diameter to close over the opening 120 of the recess 118 to form an enclosed calibration gas zone when the bellows 108 is extended. At the distal end of the bellows 108, a calibration gas input port 110 is provided for introduction of a calibration gas into the interior of the bellows 108.

As more particularly illustrated in FIG. 2, which depicts the gas calibration device assembly in calibrating position in cross sectional view, the bellows 108, the mounting plate 104, and the sintered metal diffusion disk 112 form an enclosure 202 which may be pressurized by applying the desired calibration gas to the calibration gas input port 110 when it is desired to calibrate the response of the reference and sensor elements. Upon pressurizing the internal bellows zone 202, the bellows 108 lengthens along its axis toward the upper face 120 of the sensor housing 100. The sintered metal diffusion disk 112 is accordingly caused to form a calibration gas enclosure 204 surrounding the flame arrester 102 of the sensor element, in response to application of pressurized calibration gas to the interior of the bellows 108. The illustrated bellows 108 may be desirably constructed of a suitable organopolymeric material such as poly(tetrafluorethylene) or polypropylene, or a suitable metallic material such as stainless steel or other appropriate metal or alloy. Because the bellows 108 is resilient and because the normal equilibrium position of the bellows is its retracted position as shown in FIG. 1, it will be appreciated that the application of pressurized gas to the interior of the bellows 108 causes not only the elongation of the bellows, but also the storing of mechanical energy in the bellows and the provision of a restorative force tending to close the bellows to its retracted position.

While pressurized calibration gas is supplied at the distal end of the bellows an outlet orifice 210 is provided in plate 212 at the proximal end of the bellows. Because it is contemplated that span gas containing combustible hydrocarbons may be used by the embodiment 10, the efficient use of calibration gas is important, and accordingly the orifice 210 constitutes the only location for exit of gas from the interior of the bellows 108 which has been introduced there by means of input orifice 110. In the illustrative embodiment 10, a calibration gas pressure of about 40 psig is applied to the interior of the bellows to force the disc 112 to close over the opening 120. The size of the orifice 210 is selected with respect to this predetermined operating pressure at the interior of the bellows, to achieve a desired rate of flow through the orifice 210 and from there into the calibration gas enclosure 204 formed in the cavity 118. In this regard, as indicated by the arrows shown on FIG. 2, calibration gas from the pressurized bellows internal zone 202 metered through orifice 210, flows through the central portion of the sintered metal diffusion disk 112 to provide a desired flow of calibration gas into the enclosed calibration enclosure 204. The calibration enclosure 204 surrounding and enclosing the sampling surface of the flame arrester 102 is furthermore provided with means for the outward diffusion or release of gas introduced into the enclosure 204, which in the illustrated embodiment 10 is provided by the periphery 206 of the porous sintered disk 112 the outward flow should not be substantially restrained, and appropriate openings in the disk 112 may be provided to assure that there is no substantial buildup of pressure in the enclosure 204. Accordingly, as illustrated by the arrows in FIG. 2, the pressurized calibration gas introduced into the internal bellows zone 202 is directed into the enclosed enclosure 204 surrounding the flame arrester 102 and is caused to pass from that zone in a continuous flow manner adapted to provide an atmosphere in the enclosure 204 substantially corresponding to the composition of the calibration gas upon purging of the ambient atmosphere. Desirably, the flow rate through the enclosure 204 will be in the range of from about 0.5 to about 3 liters per minute at a pressure not exceeding about 5 psi and preferably not exceeding 0.5 psi above ambient pressure to provide for accurate calibration conditions.

Upon completion of the calibration cycle, the supply of pressurized calibration gas may be stopped, and the internal pressure in the bellows will return to ambient pressure. The restorative force of the bellows will cause the bellows to return to its retracted position which in turn causes disassembly the calibration zone 204 to restore the sensor sampling access to the ambient atmosphere.

It will be appreciated from the previous description that the apparatus 10 may be utilized to pipe calibration zero and span gases to the sensor from a location that is remote from the sensor but easily accessible by a person performing a calibration. Alternatively, the calibration procedure may be centrally controlled, and the present invention facilitates such central control.

Operation of the embodiment 10 is further illustrated by FIG. 4 which schematically illustrate a calibration system 400 utilizing the assembly 10 of FIG. 1. The system 400 includes a pressurized source 402 of zero calibration gas (such as synthetic air) and a pressurized source of span calibration gas (such as a mixture of air and methane at a concentration of 50 percent of the lower flammable limit (LFL) of the methane in air) located remotely from sensor embodiment 10, but connected thereto by means of gas conduit 406. Appropriate control means 408, 410, which may be manual or automatic control elements such as valves or electro mechanical solenoids, are provided to control the application of the respective zero and span gases to the sensor 10. A typical calibration cycle for the system 400 could be carried out by turning on the source of zero gas 402 (typically clean air) by means of control element 408 and allow enough time for it to equilibrate and purge the sensor of all ambient air. The sensor response is then adjusted for a "zero" condition. The zero calibration gas may then be turned off and an appropriate span gas 404 is turned on. After enough time for the sensor to reach a final and stable reading, the sensor span is adjusted or compensated to an appropriate reading for the known concentration of the span calibration gas. The span gas supply may then be turned off and the calibration cycle is complete.

For certain sensors it may be necessary or desirable to use several combinations of calibration gas and/or zero gas. For example, it may be desirable to calibrate non-linear sensor response using concentrations of span calibration gas, such as provided by synthetic mixtures of the zero and calibration gases, which may be accomplished through appropriate flow meters or other control mechanisms.

It will be appreciated that in accordance with the present invention, calibration gas is applied from the same side of the flame arrester or dust cover as occurs during normal operation. By selecting an appropriate supply pressure for the calibration or zero gas line and an appropriate size for the orifices, a predetermined, desired flow rate to the temporarily enclosed sensor calibration zone can be generated. More specifically, an appropriate amount of gas can be supplied via appropriate flow regulation means that the sensor calibration cavity formed in response to application of the pressurized calibration gas has a concentration of span or zero gas that closely approximates an equivalent ambient condition. Since zero or span calibration gas going into the sensor calibration cavity can immediately escape to the atmosphere there is no possibility for pressure build-up in the detector cavity. Accordingly, the pressure in the detector cavity need not be substantially increased under calibration conditions, even when the flame arrester of the sensor cavity has become partially clogged. Also, should the flame arrester of the sensor become partially clogged, it is noted that there will be an accompanying loss in sensor signal realistically portraying its performance in an ambient air combustible gas concentration build-up.

A major advantage of the present invention is that it reduces the possibility for a false sensor calibration by applying gas for span or zero calibrations directly inside the detector cavity thereby circumventing any problems due to a clogged flame arrester. Span and zero gas reach the detector cavity substantially the same way as gas mixtures from the ambient environment reach the sensor.

Furthermore, by simply supplying the calibration gas the calibration fixture is caused into an appropriate position. Removal of gas pressure immediately allows the diffusion plate to retreat to its stand-by position for normal sensing of the ambient atmosphere.

Another advantage is the fail safe nature of the illustrative embodiment. For example, if the calibration gas line 406 leaks, if the bellows 108 won't expand, if cracks or fractures occur in the diffusion plate 112 or the flame arrester becomes clogged, then the detector cavity will not receive adequate calibration or zero gas flow volume for calibration. The sensor will thus tend to be "over-spanned" as a result of system malfunction so that it will read higher than actual ambient concentrations of combustible gas. While this is undesirable, it is a better alternative than being calibrated for a sensitivity than that necessary to correctly measure actual ambient concentration of combustible gas.

While the previously described embodiment 10 illustrates specific construction and use of a calibration gas utilization device in accordance with the present invention, it will be appreciated that numerous alternative embodiments may be provided based on the present disclosure. For example, an air piston or other pneumatic structure may be used to form the calibration chamber, and various other forms and shapes of bellows may also be used, as well as various other types of closure elements.

In this regard, illustrated in FIG. 3 is an alternative embodiment 300 which uses a telescoping air piston assembly 302 comprising an inner cylinder 304 and an outer cylinder 306 slidably mounted thereon, with a gas seal provided by "O" rings 308. The closure disk 310 may be made of a metal or plastic sheet or mesh with a plurality of input and exit orifices formed therein. The telescoping air piston assembly 302 includes a spring 314 which stores energy during expansion of the assembly under application of calibration gas pressure, and which provides sufficient restorative force upon removal of the calibration gas pressure to close the cylinder assembly. The restorative force of the spring may be selected to provide sufficient force to retain the telescoped cylinders to compressed position upon removal of the pressurized gas. The embodiment 300 may be adapted to operates with less calibration gas pressure to the bellows chamber than the embodiment 10 of FIG. 1, which utilizes a more relatively stiff organopolymeric bellows.

While the present invention has been specifically described with respect to specific embodiments of the invention, it will be appreciated that various modifications, variations and adaptations may be made within the spirit and scope of the present disclosure, which are intended to be within the scope of the following claims.

Various of the features of the invention are set forth in the following claims.

What is claimed is:

1. A method for application of calibration gas to a combustible gas sensor which is normally positioned in a sampling recess and which is normally exposed to the ambient atmosphere through a porous sampling surface, comprising the steps of:

applying pressurized calibration gas to the interior of a chamber which extends in response to said application of pressurized calibration gas and forming a calibration enclosure surrounding the sampling surface in mechanical response to said application by covering said recess in response to said application of pressurized calibration gas, introducing calibration gas into said calibration enclosure for calibration of said sensor, and stopping the application of pressurized calibration gas and opening the calibration enclosure to reexpose the sampling surface of the combustible gas sensor to the ambient atmosphere.

2. A method in accordance with claim 1 wherein said chamber is a bellows.

3. A method in accordance with claim 1 wherein said chamber is a telescoping chamber.

4. A method in accordance with claim 1 wherein said calibration gas is applied at a pressure in the range of from about 3 psig to about 50 psig, and wherein said calibration gas is introduced into said calibration enclosure at a flow delivery rate in the range of from about 0.5 to about 3 liters per minute.

5. Combustible gas detector calibration apparatus or the like, comprising, a combustible gas sensor having a porous sampling surface which is normally exposed to the ambient atmosphere, enclosure forming means responsive to the application of pressurized calibration gas for temporarily forming a calibration zone enclosing said sampling surface, and for opening said zone and reexposing said sampling surface upon ceasing the application of pressurized calibration gas, and means responsive to the application of pressurized calibration gas for conducting calibration gas through the calibration zone formed by said enclosure forming means.

6. A combustible gas detector calibration apparatus in accordance with claim 5 wherein said means for conducting calibration gas through the calibration zone provides a flow rate of calibration gas through the zone in the range of from about 0.3 to about 5 liters per minute.

7. A combustible gas detector calibration apparatus in accordance with claim 5 wherein said combustible gas sensor is positioned with means forming a recess and wherein said enclosure comprises a chamber which elongates in response to application of pressurized calibration gas to the interior thereof to cover said recess, said chamber including means for storing mechanical energy upon elongation which is sufficient to restore said chamber to a shortened position in the absence of pressurized gas applied to the interior thereof.

8. A combustible gas detector calibration apparatus in accordance with claim 7 wherein said chamber comprises a bellows or telescoping chamber adapted to introduce calibration gas at a pressure of less than about 0.5 psi through the calibration zone.

* * * * *